US00PP27213P2

(12) United States Plant Patent
Bullis

(10) Patent No.: US PP27,213 P2
(45) Date of Patent: Sep. 27, 2016

(54) ***NEOREGELIA* PLANT NAMED 'CASABLANCA'**

(50) Latin Name: *Neoregelia carolinae×Neoregelia×hybrida*
Varietal Denomination: Casablanca

(71) Applicant: Patricia Gomez Bullis, Princeton, FL (US)

(72) Inventor: Patricia Gomez Bullis, Princeton, FL (US)

(73) Assignee: BULLIS BROMELIADS, Princeton, FL (US)

( * ) Notice: Subject to any disclaimer, the term of this patent is extended or adjusted under 35 U.S.C. 154(b) by 70 days.

(21) Appl. No.: 14/544,214

(22) Filed: Dec. 9, 2014

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Annette Para
(74) *Attorney, Agent, or Firm* — C. A. Whealy

(57) ABSTRACT

A new and distinct cultivar of *Neoregelia* plant named 'Casablanca', characterized by its upright and outwardly arching growth habit; leaves that are mostly yellow in color with distinct dark green-colored marginal stripes and margins; uppermost leaves, proximally, purple in color; and good interiorscape and landscape performance.

1 Drawing Sheet

Botanical designation: *Neoregelia carolinae* X *Neoregelia×hybrida.*
Cultivar denomination: 'CASABLANCA'.

BACKGROUND OF THE INVENTION

The present invention relates to a new and distinct cultivar of *Neoregelia* plant, botanically known as *Neoregelia carolinae* X *Neoregelia×hybrida*, and hereinafter referred to by the name 'Casablanca'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia carolinae*, not patented, as the female, or seed, parent with an unnamed proprietary selection of *Neoregelia×hybrida*, not patented, as the male, or pollen, parent. The new *Neoregelia* plant was discovered and selected by the Inventor as a single plant within the progeny of the stated cross-pollination in a controlled greenhouse environment in Princeton, Fla. in 2003.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible combinations of environmental conditions and cultural practices. The phenotype may vary somewhat with variations in environment conditions such as temperature and light intensity without, however, any variance in genotype.

The following traits have been repeatedly observed and are determined to be the unique characteristics of 'Casablanca'. These characteristics in combination distinguish 'Casablanca' as a new and distinct *Neoregelia* plant:

1. Upright and outwardly arching growth habit.
2. Leaves that are mostly yellow in color with distinct dark green-colored marginal stripes and margins; uppermost leaves, proximally, purple in color.
3. Good interiorscape and landscape performance.

Plants of the new *Neoregelia* differ primarily from plants of the female parent selection in the following characteristics:

1. Leaf coloration of plants of the new *Neoregelia* is more stable than leaf coloration of plants of the female parent selection.
2. Plants of the new *Neoregelia* and the female parent selection differ in leaf color as plants of the female parent selection have orange-colored leaves.

Plants of the new *Neoregelia* differ primarily from plants of the male parent selection in the following characteristics:

1. Plants of the new *Neoregelia* have narrower leaves than plants of the male parent selection.
2. Plants of the new *Neoregelia* and the male parent selection differ in leaf color as plants of the male parent selection have green-colored leaves.

Plants of the new *Neoregelia* can be compared to plants of the *Neoregelia* 'Tri-color', not patented. In side-by-side comparisons conducted in Princeton, Fla., plants of the new *Neoregelia* and 'Tri-color' differed primarily in the following characteristics:

1. Leaf coloration of plants of the new *Neoregelia* was more stable than leaf coloration of plants of 'Tri-color'.
2. Plants of the new *Neoregelia* and 'Tri-color' differed in leaf color as plants of 'Tri-color' were yellow green and green in equal areas.

3. Plants of the new *Neoregelia* were more tolerant to root rot pathogens than plants of 'Tri-color'.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Casablanca' grown in a container.

The photograph at the top of the sheet is a top perspective view of a typical flowering plant of 'Casablanca'.

DETAILED BOTANICAL DESCRIPTION

The aforementioned photographs and following observations, measurements and values describe flowering plants grown during the spring and summer in 15-cm containers in a polypropylene-covered greenhouse in Princeton, Fla. and under cultural practices typical of commercial *Neoregelia* production. During the production of the plants, day temperatures ranged from 28° C. to 30° C., night temperatures ranged from 18° C. to 22° C. and light levels averaged 3,200 foot-candles. Plants were 13 months old when the photographs and description were taken. In the following description, color references are made to The Royal Horticultural Society Colour Chart, 2007 Edition, except where general terms of ordinary dictionary significance are used.

Botanical classification: *Neoregelia carolinae* X *Neoregelia×hybrida* 'Casablanca'.

Parentage:

*Female, or seed, parent*.—Unnamed proprietary selection of *Neoregelia carolinae*, not patented.

*Male, or pollen, parent*.—Unnamed proprietary selection of *Neoregelia×hybrida*, not patented.

Propagation:

*Type*.—By offsets.

*Time to initiate roots, summer*.—About 30 to 40 days at temperatures about 28° C. to 30° C.

*Time to initiate roots, winter*.—About 45 to 55 days at temperatures about 28° C. to 30° C.

*Time to produce a rooted young plant, summer*.—About three months at temperatures about 28° C. to 30° C.

*Time to produce a rooted young plant, winter*.—About four months at temperatures about 18° C. to 22° C.

*Root description*.—Medium in thickness, fibrous; yellow to beige tan in color.

*Rooting habit*.—Moderately freely branching; medium density.

Plant description:

*Plant and growth habit*.—Upright and outwardly arching growth habit; rosette leaves are erect when young, becoming outwardly arching with development; plants readily produce uniform offsets; vigorous growth habit.

*Plant height*.—About 17.5 cm.

*Plant diameter or spread*.—About 44 cm.

*Internode length*.—About 4.5 mm.

*Stem texture*.—Smooth, glabrous.

*Stem color*.—Close to NN155A.

Leaf description:

*Arrangement*.—Rosette, spiral phyllotaxis; simple; sessile, clasping.

*Shape*.—Oblong with broad sheathing base.

*Apex*.—Cuspidate.

*Base*.—Truncate.

*Margin*.—Serrate, spinose.

*Length*.—About 31 cm.

*Width, mid-section*.—About 5.3 cm.

*Width, base*.—About 7.4 cm.

*Texture, upper and lower surfaces*.—Smooth, glabrous; leathery; longitudinally ribbed.

*Luster, upper and lower surfaces*.—Glossy, shiny.

*Venation pattern*.—Parallel.

*Color*.—Lower leaves, upper surface: Broad centers, lighter than 153A; longitudinal marginal stripes and margins, close to 147A to 147B; midrib, close to N137A. Lower leaves, lower surface: Broad centers, lighter than 153A; longitudinal marginal stripes and margins, close to 147A and N137A; midrib, close to 153A. Upper leaves, upper surface: Broad centers, close to 160B; longitudinal marginal stripes and margins, close to 139A and 137A to 137B; towards the base, close to 157A; midrib, close to 160B; uppermost leaves subtending the inflorescence are proximally close to 186A in color. Upper leaves, lower surface: Broad centers, close to 160C; longitudinal marginal stripes and margins, close to 137A to 137B; midrib, close to 160C.

Inflorescence description:

*Inflorescence form*.—Terminal flat-topped compact corymb located inside the leaf rosette; about 110 flowers develop per inflorescence.

*Time to flower*.—Plants begin flowering about eight to ten weeks after planting; plants flower naturally during the spring in Florida.

*Flower longevity*.—Individual flowers last about one to two days on the plant; flowers persistent.

*Fragrance*.—None detected.

*Inflorescence length*.—About 6.4 cm.

*Inflorescence diameter*.—About 4.8 cm.

*Flower size*.—Length: About 4.6 cm. Diameter: About 8 mm.

*Flower buds*.—Length: About 4.1 cm. Diameter: About 5 mm. Shape: Narrowly elongate. Color: Close to 91B.

*Petals*.—Quantity per flower: Three in a single whorl. Shape: Oblanceolate. Apex: Acute. Base: Truncate. Margin: Entire. Length: About 3.3 cm. Width: About 6 mm. Texture, upper and lower surfaces: Smooth, glabrous. Color: When opening, upper (inner) surface: Close to 93B. When opening, lower (outer) surface: Close to 93C to 93D. Fully opened, upper (inner) surface: Close to 93B to 93C; towards the base, close to NN155D. Fully opened, lower (outer) surface: Close to 93D; towards the base, close to NN155D.

*Flower bracts*.—Quantity per flower: One. Shape: Elliptical. Length: About 3.3 cm. Width: About 8 mm. Texture, upper and lower surfaces: Membraneous. Color, upper and lower surfaces: Close to 157B to 157D.

*Sepals*.—Quantity per flower: Three in a single whorl. Shape: Oblanceolate. Apex: Acuminate. Base: Truncate. Margin: Entire. Length: About 2.6 cm. Width:

About 5 mm. Texture, upper and lower surfaces: Smooth, glabrous. Luster, upper and lower surfaces: Glossy, shiny. Color, upper and lower surfaces: Close to 146C to 146D; towards the base, close to 145D.

*Peduncles*.—Length: About 1.1 cm. Diameter: About 1.6 cm. Strength: Strong. Aspect: Typically erect. Texture: Smooth, glabrous. Color: Close to NN155D.

*Pedicels*.—Length: About 9 mm. Diameter: About 3 mm. Strength: Strong. Aspect: Typically erect to outward and curving upright. Texture: Smooth, glabrous. Color: Close to NN155D.

*Stamens*.—Quantity per flower: Six. Filament length: About 1.8 cm; partially adnate to the petals. Filament color: Close to NN155D. Anther shape: Lanceolate. Anther length: About 4 mm. Anther color: Close to 158C. Pollen amount: Scarce. Pollen color: Close to 158A.

*Pistils*.—Quantity per flower: One. Pistil length: About 3.2 cm. Stigma shape: Oval, elongated. Stigma color: Close to NN155B. Style length: About 1.8 cm. Style color: Close to NN155D. Ovary color: Close to NN155D.

*Fruits and seeds*.—To date, fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance. Plants of the new *Neoregelia* have been observed to tolerate summer rains.

Pathogen & pest tolerance/resistance: Plants of the new *Neoregelia* have been observed to be somewhat tolerant to root rot pathogens such as *Pythium* and *Phytophthora*. Tolerance and resistance to pests and other pathogens common to *Neoregelia* plants has not been observed.

It is claimed:

1. A new and distinct *Neoregelia* plant named 'Casablanca' as illustrated and described.

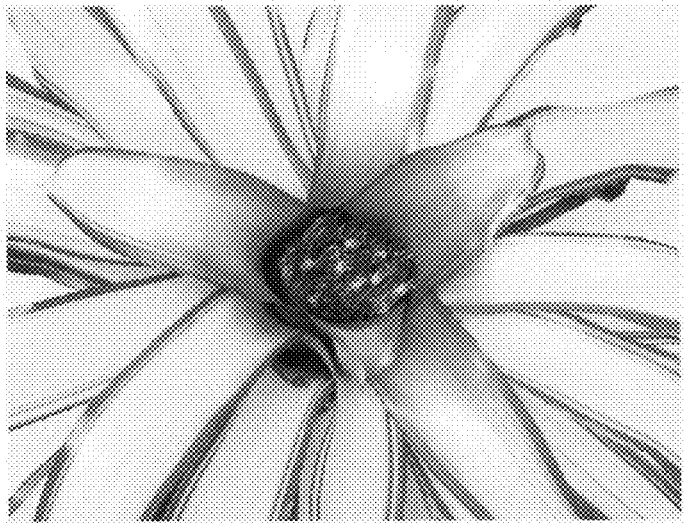
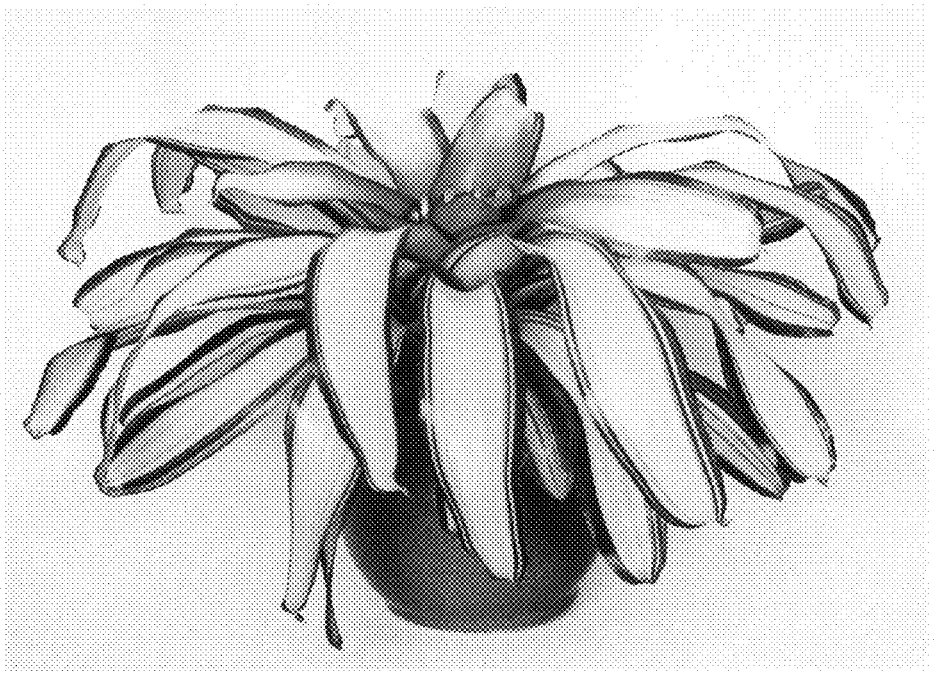

* * * * *